US010517475B2

(12) United States Patent
Satgunam et al.

(10) Patent No.: US 10,517,475 B2
(45) Date of Patent: Dec. 31, 2019

(54) APPARATUS AND A METHOD THEREWITH TO QUANTIFY VISUAL PATTERNS IN INFANTS

(71) Applicant: Hyderabad Eye Research Foundation, Hyderabad, Telangana (IN)

(72) Inventors: Premnandhini Satgunam, Telangana (IN); B Karthik Reddy, Telangana (IN); Dhruv Joshi, Maharashtra (IN); Nidumolu Koudinya, Telangana (IN); Sourav Datta, West Bengal (IN)

(73) Assignee: Hyderabad Eye Research Foundation, Hyderabad, Telangana (IN)

( * ) Notice: Subject to any disclaimer, the term of this patent is extended or adjusted under 35 U.S.C. 154(b) by 50 days.

(21) Appl. No.: 15/566,618

(22) PCT Filed: Jul. 12, 2016

(86) PCT No.: PCT/IB2016/054148
§ 371 (c)(1),
(2) Date: Oct. 13, 2017

(87) PCT Pub. No.: WO2017/029563
PCT Pub. Date: Feb. 23, 2017

(65) Prior Publication Data
US 2018/0103840 A1    Apr. 19, 2018

(30) Foreign Application Priority Data
Aug. 19, 2015   (IN) .......................... 4341/CHE/2015

(51) Int. Cl.
*A61B 3/024*   (2006.01)
*A61B 3/00*    (2006.01)
(Continued)

(52) U.S. Cl.
CPC ............ *A61B 3/024* (2013.01); *A61B 3/0033* (2013.01); *A61B 3/0041* (2013.01); *A61B 3/18* (2013.01);
(Continued)

(58) Field of Classification Search
CPC .................................................... A61B 3/0245
(Continued)

(56) References Cited

U.S. PATENT DOCUMENTS

| 8,500,278 | B2 * | 8/2013 | Lo | A61B 3/024 351/206 |
| 2014/0240675 | A1 * | 8/2014 | Narasimha-Iyer | A61B 3/0091 351/210 |
| 2016/0249798 | A1 * | 9/2016 | Mantysalo | A61B 3/0091 351/224 |

FOREIGN PATENT DOCUMENTS

WO    WO2008052166 A2    5/2008

\* cited by examiner

*Primary Examiner* — Robert E. Tallman
(74) *Attorney, Agent, or Firm* — Bret E. Field; Bozicevic, Field & Francis LLP (57) ABSTRACT

The invention relates to an apparatus and a method therewith to quantify visual field in infants. The invention provides a novel solution to the unmet need of detection of defects in the visual field in infants and/or babies and providing an apparatus with a software framework to minimize the errors of recording the readings and increasing their precision and analyzing said results automatically using the software embedded in the system. Said apparatus to quantify visual field in infants comprise of a light projection device onto a dome-shaped hemispherical structure with an infra-red camera along with fixation lights, a means for monitoring responses of the subject during testing, a means for recording and analyzing the readings. Said means to detect and record the eye/head movement in the subject during testing
(Continued)

comprises said infra red (IR) camera connected to a device wherein software application is embedded.

18 Claims, 7 Drawing Sheets

(51) Int. Cl.
    *A61B 3/18*         (2006.01)
    *A61B 3/113*       (2006.01)

(52) U.S. Cl.
    CPC .............. *A61B 3/0008* (2013.01); *A61B 3/113* (2013.01); *A61B 2503/04* (2013.01)

(58) Field of Classification Search
    USPC ........................................ 351/222, 224, 226
    See application file for complete search history.

APPARATUS AND A METHOD THEREWITH TO QUANTIFY VISUAL PATTERNS IN INFANTS

FIELD OF INVENTION

The invention relates to an apparatus and a method, mainly a pediatric perimeter, for quantifying visual fields in infants. The invention explains a novel method for determining visual fields in infants using a software framework to reduce the incurred error with traditional methods by providing automatic and accurate recording of reading and analyzing said results. Also the testing condition provides more comfortable viewing without disturbing an infant's natural behavioral movements.

DESCRIPTION OF THE RELATED ART/BACKGROUND

'Visual field' is the extent of side vision (or peripheral vision) of a person while looking straight ahead. A device used to measure the extent or gaps in the visual field is called a 'perimeter'. The perimeter testing serves as a screening tool to detect diseases of the eye and the visual pathway that connects the eye to the brain. Testing the visual fields is as important in children as it is in adults as there are several diseases that occur in both age groups affecting the visual fields (e.g. glaucoma, hemianopia). It is also known that many children with multiple disabilities (e.g. cerebral palsy) also have visual field defects.

State-of-the-art perimetric testing requires an individual to be seated with the head and chin firmly placed in the device and to respond to the detection of a moving/flashed light with a button press.

U.S. application Ser. No. 13/959,295 describes imaging method using an eye examining instrument wherein a projecting device projects a beam onto the convex reflector and the beam is reflected by the convex reflector onto the concave screen imaged on the concave screen, different objects of various sizes and shape are imaged on the screen. The subject can operate a push button when he/she sees the image.

This becomes cumbersome for the children to keep clicking the button and in case of infants it is not practical to take readings using said device. Thus what is needed is a novel solution for measuring visual field in infants and children. The pediatric perimeter can be used to determine the outer boundaries of the visual field, more particularly measuring the said visual field.

The invention discloses a pediatric perimeter with a simple interface communicating with software operating on an embedded low-power computer system.

OBJECT OF THE INVENTION

The principal object of the invention is to provide a novel solution to the unmet need of detection of visual field defects in infants and providing an apparatus with a software framework to minimize the errors of recording the reading.

Another object of the invention is to provide a low cost, portable apparatus affordable to every patient.

Yet another object of this invention is to address the eye health needs of neonates and children, and control childhood blindness through government programs on child health screening and early intervention services.

Further object of the invention is to provide an automated recording and analyzing the readings using software implementation in said apparatus.

SUMMARY OF THE INVENTION

In one embodiment of the invention disclosed herein is an apparatus and a method therewith to quantify visual pattern in infants that comprises a projection device with at least one camera along with an illumination source, wherein said camera can be infra red and said illumination sources can be an infra red light source, fixation lights, a means for monitoring responses of the subject during testing, a means for recording and analyzing the readings wherein said IR camera helps feed a live video of the subject during testing in complete darkness or low ambient lighting and LEDs are attached beside the camera on the top of the hemispherical dome.

In yet another embodiment of the invention said means for monitoring responses of the subject during the testing comprises graphical user interface and a key press to control the light stimulus. Wherein said means for recording and analyzing said readings to quantify the results include software embedded in the computer system wherein said software records the changes in the visual pattern of the subject and analyses the recorded results.

DETAIL DESCRIPTION OF THE INVENTION

The invention disclosed herein describes an apparatus and a method therewith to measure and quantify visual fields in babies. The invention helps in testing side vision in infants using a programmable light source such as patterned LED arrays or a projector that are projected along the inner surface of the device, mainly a hemispherical dome-shaped structure either collapsible or non collapsible and recording the subject's visual pattern, in this case infants.

Said apparatus is linked with customized software on a device wherein said software records the response to the visual pattern of the subject and, analyses the recorded results. The recorded results are also manually analyzed by the examiner. The infra red camera placed at the top center of the dome shaped device visualizes the subject's face on the computer screen, enabling the tracking of the subject's gaze and permitting the examiner to observe the subject.

The illuminated meridians on the hemispherical dome for light stimuli are selected manually. Light with a wavelength of 580 nm is used but not limited to that mentioned since this wavelength is closer to 555 nm the wavelength that has the maximum sensitivity to human eyes. Upon detection of an eye/head movement the field angle extent is registered by the examiner or the registration process can be automated through the software.

In another embodiment the meridians are detected by the software framework embedded in the device and are illuminated on the concave inner surface of the hemispherical dome shaped device covering the entire visual field, half of it or a quarter, depending upon the testing paradigm.

The hemispherical dome with light source is meant for light stimuli along with an IR camera at the top to visualize subjects face on the GUI (Graphical User Interface). Said GUI has a video display and a means to control the light in the dome. Said GUI consists of three primary components mainly, a. The panel for entering patient data wherein patent details are entered.
b. Live streaming of the video feed from camera and text that gives the present testing status.
c. Light source controls depending on the gaze fixation of the infant by the examiner and controlling light stimulus with key press.

Said method includes fixation of the zero level of the infant's vision wherein said zero level is the fixed gaze for the infant such that the examiner gets the zero point with respect to which to examine the responses, on fixating the gaze, the light stimuli is supplied on the concave inner surface of the hemispherical dome, covering the entire surface or part of it depending on the testing paradigm. Fixing the gaze is very important for the infant since it would serve as a reference point for mapping visual field reading accurately. In another embodiment of the invention, wherein the baby does not fixate at the zero level, said invention uses a predefined high contrast pattern worn on the subject's head in the form of a cap/headband during the testing. These patterns would be identified by the cameras) and the software determines accurately the orientation of the head and the eyes of the subject. Said Hemisphere is defined as one half of the dome and said quadrant is termed as one quarter of the dome. Individual meridians on said device are lighted by clicking on the particular meridian.

Said GUI comprises panel for text entry and buttons to save the patient data before starting the test, the live feed from the camera is displayed on the screen once the patient data is entered, the examiner fixates the gaze at the center where four LEDs are placed.

The status text just below the video gives the dynamic status of the test running. Moreover, the brightness and the velocity of light stimulus can be controlled during kinetic perimetry wherein brightness is controlled by setting the level on the slider and delay is altered by entering the delay duration in milliseconds and then clicking on the send button beside the video. The video stream has the water mark to adjust the reference point for fixating the vision of babies.

Depending upon the current status of the gaze and the cooperation of the subject the test is carried out. Live feedback of the status of the light stimulus is updated dynamically on the screen.

Detailed analysis and reports are generated after the test that includes a video file, a text file along with detailed report that include patient data, detailed information on the type of test and parameters generated as a consequence of the response of the baby and additional features tested on the patient (brightness and delay). Furthermore, an Isopter image generated after the test, showing a visualization of the visual field. Visual field Isopter is the line connecting the points of visual field extension in each meridian.

Example

Six infants with developmental delay (DD) and 3 children with normal milestones (NM) were tested. The mean age of the DD group is 12.96±6.53 months and 3 NM infants were 7 months of age (two babies) and one child of 2 years old. The two year old child was tested as a control subject for his twin sister who had DD.

Figure 1:
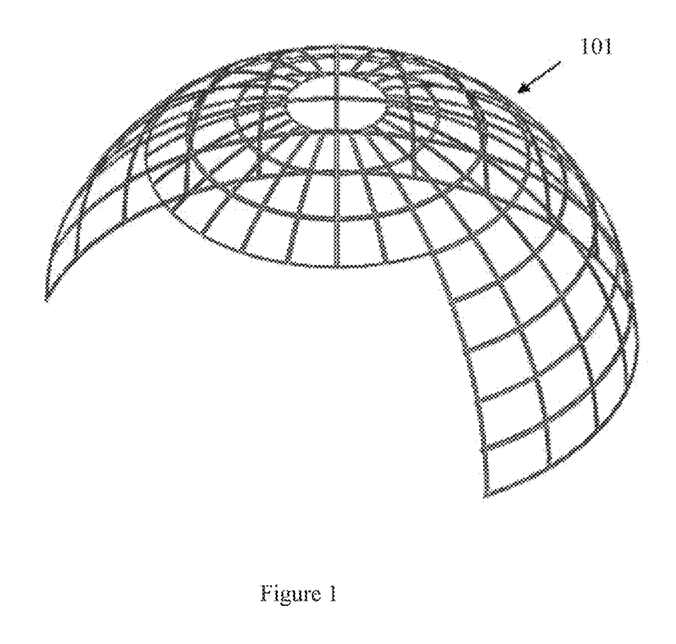
FIG. 1 illustrates a hemispherical dome (100) for attachment of light stimuli and infra red camera and LED lights.
Figure 2:
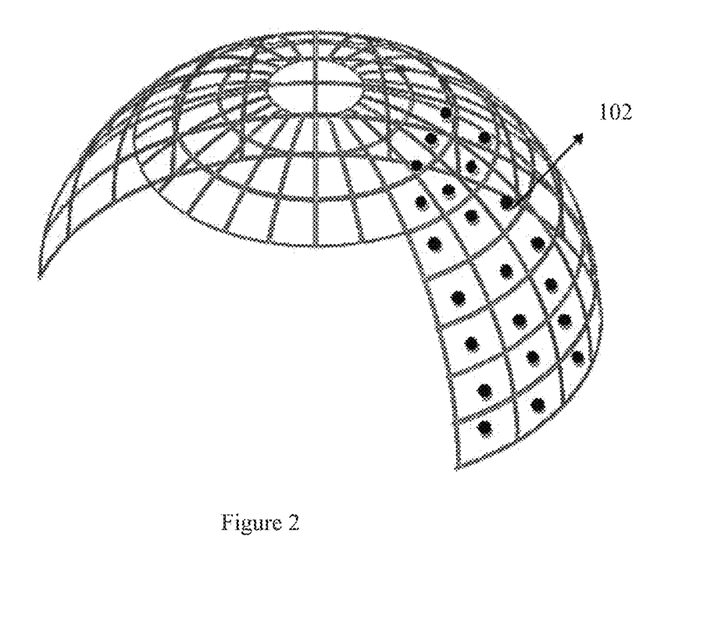
FIG. 2 illustrates said hemispherical dome with multiple LED lights (102) attached, the brightness of the light and the delay of turning the lights on is controlled manually.
Figure 3:
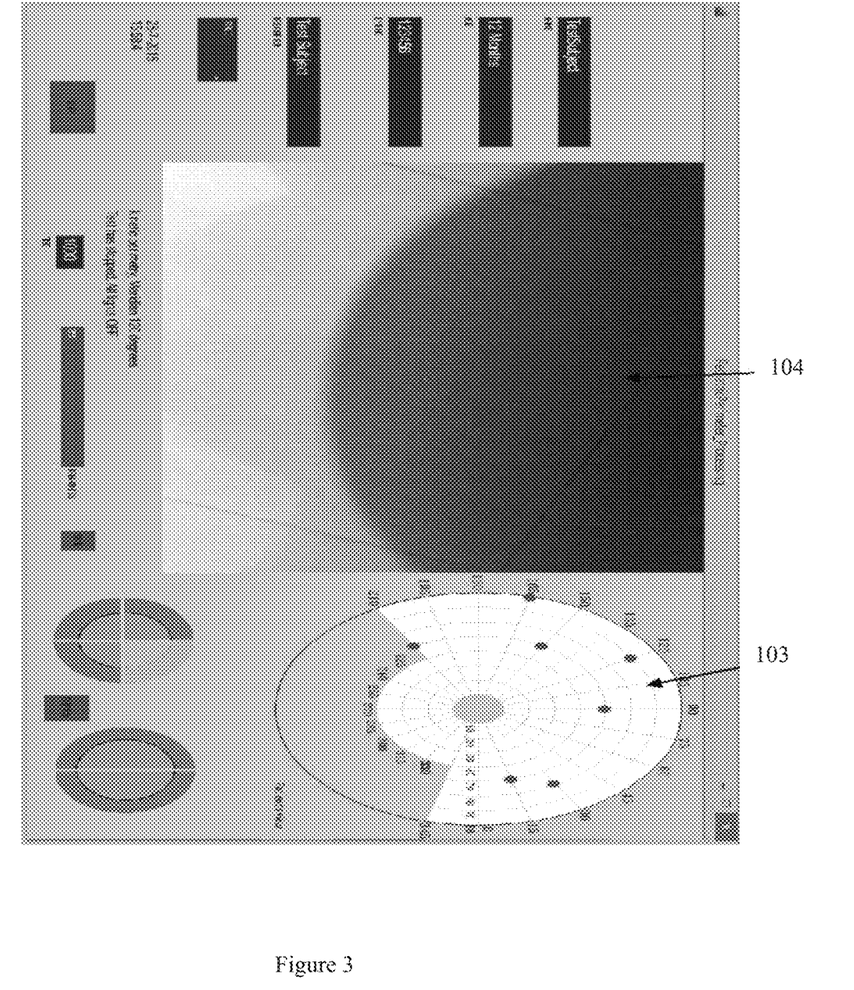
FIG. 3 illustrates screenshot of the graphical user interface wherein visual screen (104) and set meridian (103) is shown wherein the live feed of the subject's moments is visualized and considered for setting the gaze and recording readings during the experiment.
Figure 4:
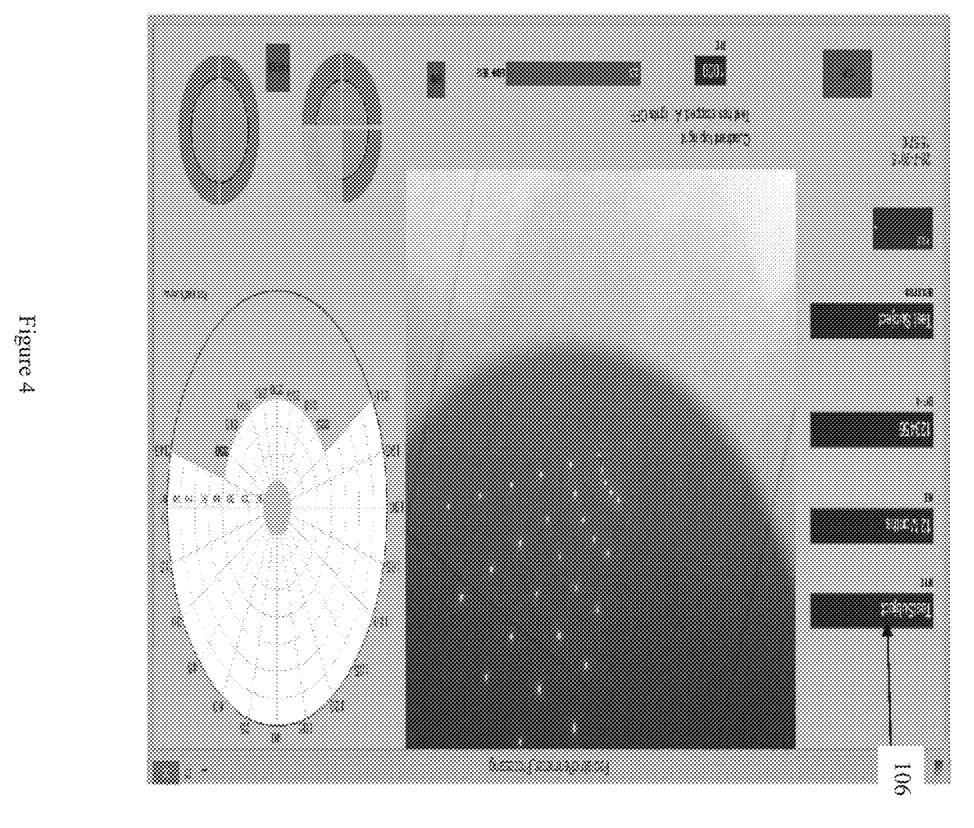
FIG. 4 illustrates graphical user interface showing LEDs lighted in the meridian and the panel (106) subject's data like age, name, patient number etc is entered.
Figure 5:
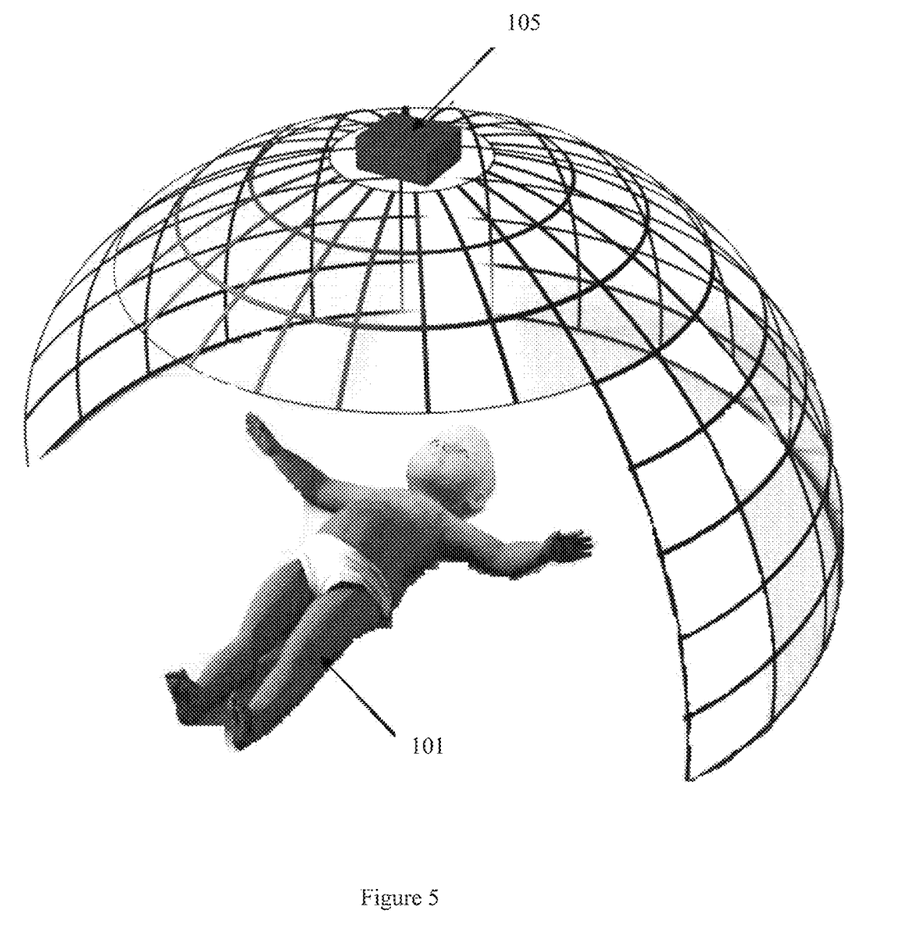
FIG. 5 illustrates the subject (101) placed under the hemispherical dome for testing and the infra red camera (105) on the top of the hemispherical dome along with four fixating lights to demonstrate the working of the invention.
Figure 6:
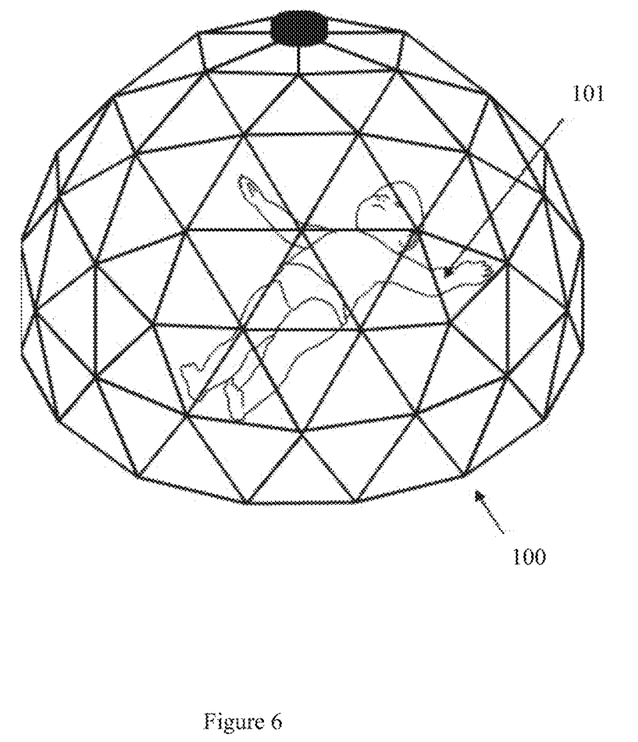
FIG. 6 illustrates the collapsible or foldable hemispherical dome with IR camera and subject for testing.
Figure 7A:
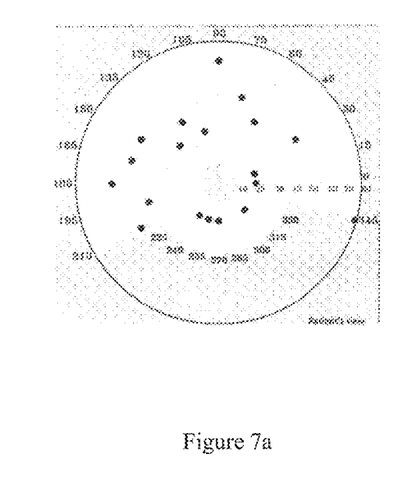
FIGS. 7a and 7b illustrate exemplary representation of visual field Isopter of the DD infants in accordance with some embodiments of the present disclosure.
Figure 7B:
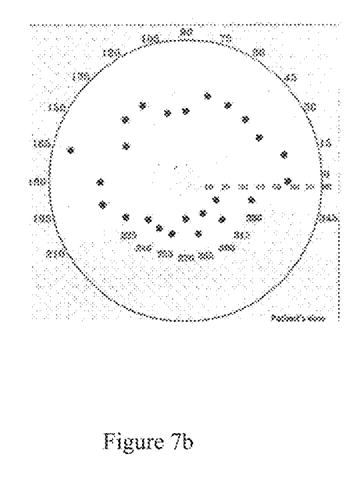

Hemi fields, quadra fields and individual meridians (n=24) were tested. NM infants did not complete all the meridians. 4 infants with DD completed all the meridians as illustrated in FIGS. 7a and 7b.

The DD infants took 6 to 25 minutes to complete the full test. The NM infants took 1.8 to 10 minutes. Out of the 6 DD infants 5 underwent early intervention therapy before perimetry testing.

The mean reaction time of the DD infants to respond to the hemispheres and the quadrants during the testing was 3.3±1.5 seconds. The NM infants' mean reaction time was 1.4±0.39 seconds.

This pilot testing demonstrates a potential for the pediatric perimeter to be used for visual field testing in infants.

The reaction time of the DD infants was about 2 times more than the infants with NM in response to the quadrants and hemispheres during the testing. However, further study is needed with more infants (both NM and DD) to understand the clinical implications. An 'NM infant' relates to infants with normal milestones and 'DD infant' relates to infants with developmental delays.

The invention claimed is:

1. An apparatus to quantify visual fields in babies and children with developmental delay, the apparatus comprising:
a projection device with at least one camera, a camera light source for the at least one camera, and a fixation light source,
a monitor for monitoring responses of the subject during testing, and
a recorder for recording and analyzing the responses,
wherein analyzing the responses includes determining gross visual field estimate, mapping visual field extent of the subject, and determining an actual time taken by the subject to look at each meridian of the projection device.

2. The apparatus according to claim 1, wherein said projection device is a hemispherical dome shaped structure with a light source to display light stimuli from a concave inner surface of the hemispherical dome.

3. The apparatus according to claim 2, wherein said hemispherical dome is foldable.

4. The apparatus according to claim 1, wherein said monitoring includes video monitoring through a graphical user interface on a computer device and registering said response using a key press that serves to record the responses.

5. The apparatus according to claim 1, wherein said at least one camera is an infrared camera that enables visualizing the subject's face and gaze on said recorder through software.

6. The apparatus according to claim 5, wherein said software selects desired visual angle to display the light stimulus for testing.

7. The apparatus according to claim 6, wherein said light stimuli is turned on at meridians from said visual angle, wherein the meridians are selected by at least one of manually by an examiner and automatically, and the response of the subject is noted.

8. The apparatus according to claim 7, wherein said response includes at least one of eye and head movement of the subject and on making any such movement or response to the light stimuli, the examiner registers said response with said key press.

9. The apparatus according to claim 1, wherein said analysis is carried out using patterns worn on the subject's head for gaze calibration.

10. A method of quantifying visual fields in babies and children with developmental delay, the method comprising:
    testing a subject with a projection device with at least one camera, a camera light source for the at least one camera, and a fixation light source,
    monitoring responses of the subject during testing, and recording and analyzing the responses,
    wherein analyzing the responses includes determining gross visual field estimate, mapping visual field extent of the subject, and determining an actual time taken by the subject to look at each meridian of the projection device.

11. The method according to claim 10, wherein said projection device is a hemispherical dome shaped structure with a light source to display light stimuli from a concave inner surface of the hemispherical dome.

12. The method according to claim 11, wherein said hemispherical dome is foldable.

13. The method according to claim 10, wherein said monitoring includes video monitoring through a graphical user interface on a computer device and registering said response using a key press that serves to record the responses.

14. The method according to claim 10, wherein said at least one camera is an infrared camera that enables visualizing the subject's face and gaze on a recorder through software.

15. The method according to claim 14, wherein said software selects desired visual angle to display the light stimulus for testing.

16. The method according to claim 15, wherein said light stimuli is turned on at meridians from said visual angle, wherein the meridians are selected by at least one of manually by an examiner and automatically, and the response of the subject is noted.

17. The method according to claim 16, wherein said response includes at least one of eye and head movement of the subject and on making any such movement or response to the light stimuli, the examiner registers said response with said key press.

18. The method according to claim 10, wherein said analysis is carried out using patterns worn on the subject's head for gaze calibration.

\* \* \* \* \*